US012076810B2

(12) United States Patent
Ogawa et al.

(10) Patent No.: US 12,076,810 B2
(45) Date of Patent: Sep. 3, 2024

(54) MANUFACTURING METHOD OF MULTILAYER SYRINGE BARREL

(71) Applicant: MITSUBISHI GAS CHEMICAL COMPANY, INC., Tokyo (JP)

(72) Inventors: Shun Ogawa, Kanagawa (JP); Shota Arakawa, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 541 days.

(21) Appl. No.: 17/282,510

(22) PCT Filed: Aug. 14, 2019

(86) PCT No.: PCT/JP2019/031939
§ 371 (c)(1),
(2) Date: Apr. 2, 2021

(87) PCT Pub. No.: WO2020/070982
PCT Pub. Date: Apr. 9, 2020

(65) Prior Publication Data
US 2021/0379692 A1    Dec. 9, 2021

(30) Foreign Application Priority Data
Oct. 4, 2018    (JP) ................. 2018-188732

(51) Int. Cl.
*B23K 26/00*     (2014.01)
*A61M 5/31*     (2006.01)
*B23K 26/38*     (2014.01)

(52) U.S. Cl.
CPC ....... *B23K 26/0093* (2013.01); *A61M 5/3129* (2013.01); *B23K 26/38* (2013.01); *A61M 2207/00* (2013.01)

(58) Field of Classification Search
CPC ... B23K 26/0093; B23K 26/38; A61M 5/3129
See application file for complete search history.

(56) References Cited

U.S. PATENT DOCUMENTS

| 10,220,150 | B2 | 3/2019 | Ito et al. |
| 2011/0100178 | A1 | 5/2011 | Tanaka |
| 2016/0325045 | A1 | 11/2016 | Ito et al. |

FOREIGN PATENT DOCUMENTS

| EP | 3106283 | A1 |   | 12/2016 |
| JP | 3780758 |   | * | 5/2006 |

(Continued)

OTHER PUBLICATIONS

International Search Report issued in International Patent Application No. PCT/JP2019/031939, dated Sep. 17, 2019, along with English translation thereof.

(Continued)

*Primary Examiner* — Mathieu D Vargot
(74) *Attorney, Agent, or Firm* — Greenblum & Bernstein, P.L.C.

(57) ABSTRACT

A manufacturing method of a multilayer syringe barrel is provided and includes: a finish cutting a remaining gate of a nozzle portion of a multilayer syringe barrel that is injection-molded from a nozzle tip, with a cutting blade of an ultrasonic cutting apparatus including a mechanism for suppressing abnormal vibration; and irradiating a laser beam to a corner portion of the nozzle portion, the corner portion being formed during the finish cutting.

10 Claims, 5 Drawing Sheets

(56) References Cited

FOREIGN PATENT DOCUMENTS

| | | |
|---|---|---|
| JP | 2016-19619 A | 2/2016 |
| JP | 2017-177444 A | 10/2017 |
| KR | 10-2016-0120715 A | 10/2016 |
| TW | 201538191 A | 10/2015 |
| WO | 2006/133044 A | 12/2006 |
| WO | 2009/084093 A1 | 7/2009 |
| WO | 2015/119284 A1 | 8/2015 |

OTHER PUBLICATIONS

Written Opinion of the International Searching Authority issued in International Patent Application No. PCT/JP2019/031939, dated Sep. 17, 2019, along with English translation thereof.

* cited by examiner

[Fig. 1]
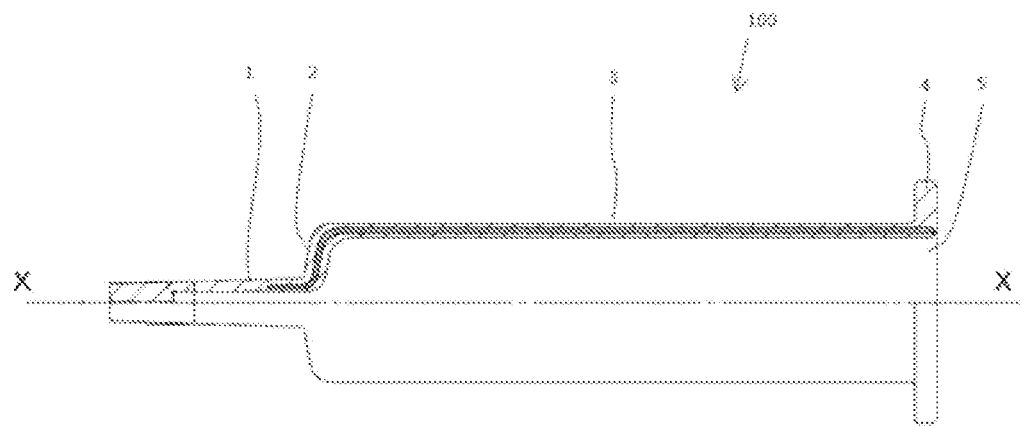
[Fig. 2]
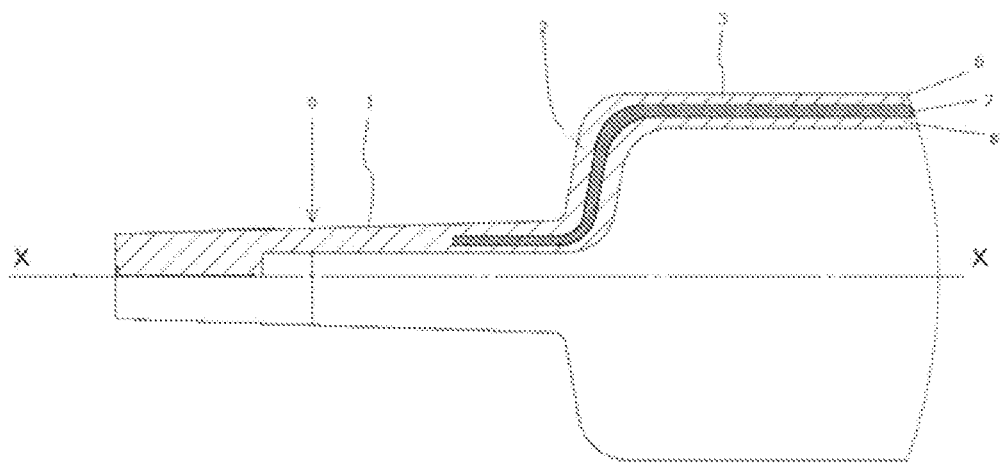

[Fig. 3]
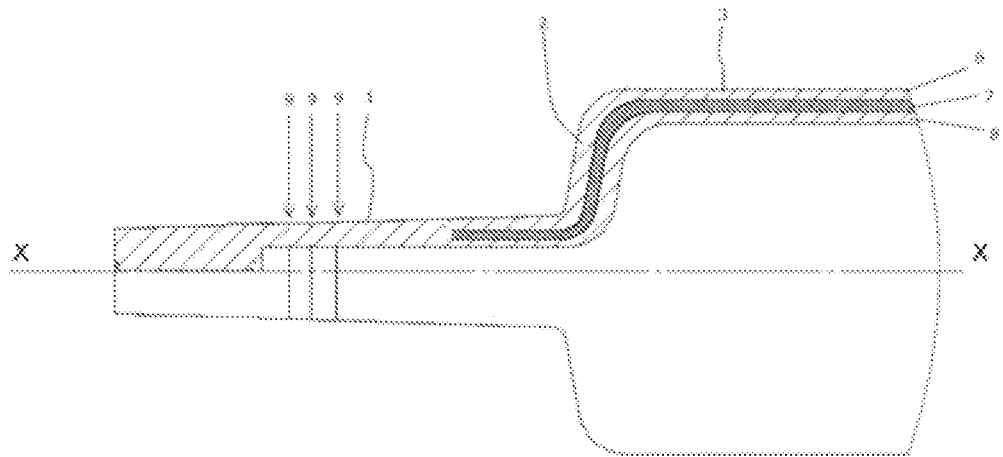
[Fig. 4]
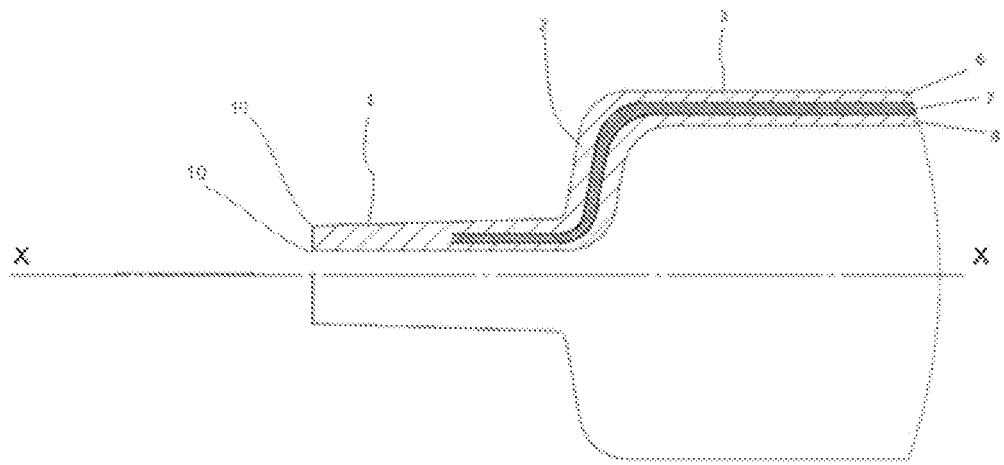
[Fig. 5]
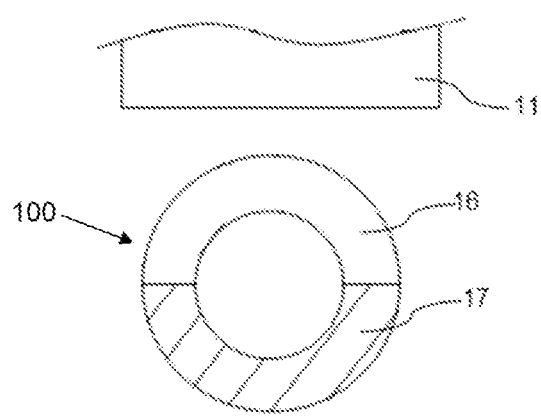

[Fig. 6]
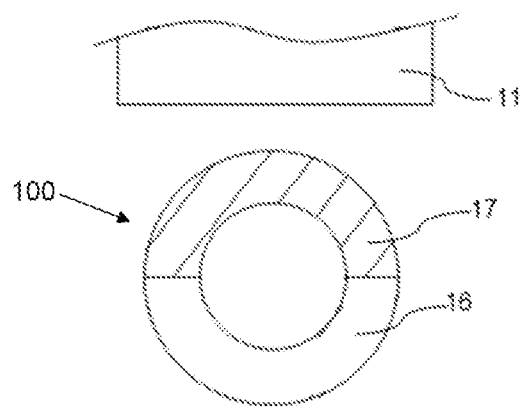
[Fig. 7]
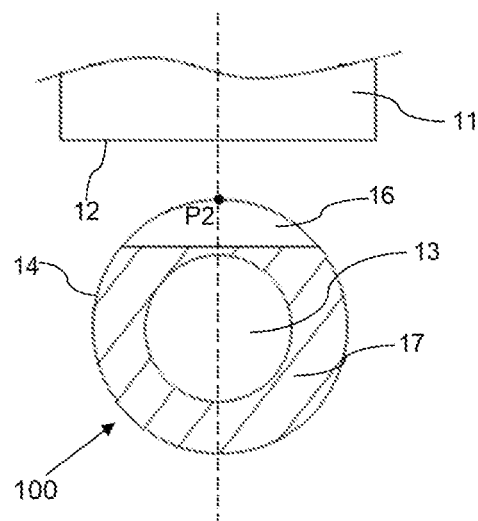

[Fig. 8]
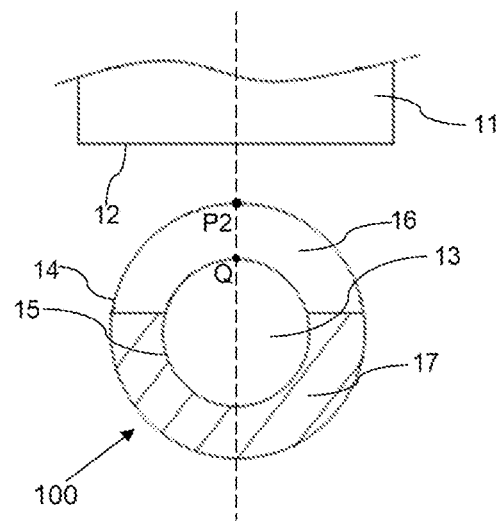
[Fig. 9]
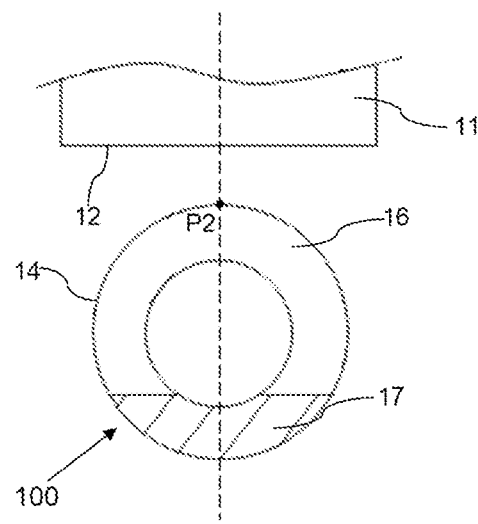

[Fig. 10]
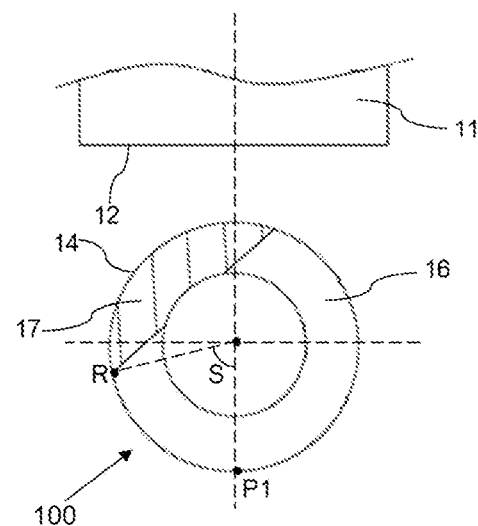

MANUFACTURING METHOD OF MULTILAYER SYRINGE BARREL

TECHNICAL FIELD

The present invention relates to a manufacturing method of a multilayer syringe barrel, and particularly relates to a manufacturing method of a multilayer syringe barrel that suppresses the generation of burrs and rolled-up parts and the multilayer structure peeling at the time of cutting of a nozzle tip of the multilayer syringe barrel, and that does not leave a pointed corner portion at a cut portion that may damage a cap.

BACKGROUND ART

Conventionally, glass pre-filled syringes are used as medical packaging containers for filling and storing a liquid medicament in a sealed state at medical fields, and the like. A pre-filled syringe is an injector in which a syringe is filled in advance with a liquid medicament required for medical treatment, and that is configured to remove a cap fitted to a cylinder tip (hereinafter referred to as "the injection portion") of the syringe barrel from which the liquid medicament is injected, and to attach a needle to the injection portion. In the pre-filled syringe, the operation of once sucking the liquid medicament stored in an ampule or vial by the syringe is unnecessary. Therefore, when the pre-filled syringe is used, it is expected that the product tampering of a liquid medicament is prevented, the efficiency of medical operations is improved, medical accidents such as incorrect administration of the liquid medicament are prevented, and the like. Conventionally, glass has been used for syringe barrels used for pre-filled syringes or the like.

However, in the case of glass pre-filled syringes, there have been problems, such as sodium ions and the like leaching into the content liquid of a container during storage, microscopic materials called flakes being generated, a metal for coloring being mixed into the content when a light-shielding glass container colored with the metal is used, and easily broken due to impact by falling or the like. Additionally, there has also been a problem that pre-filled syringes become heavy, since glass has a relatively high specific gravity.

In order to solve the above problems, the technology using a thermoplastic resin, which is lighter compared with glass, are being considered as a glass substitute used for a syringe barrel. As a pre-filled syringe using such a thermoplastic resin, the present inventors have proposed a container for pre-filled syringe that has the layered structure of a resin layer and an oxygen barrier layer, and has excellent oxygen barrier properties (for example, refer to the following Patent Literature 1). In addition, when the multilayer syringe as described above is manufactured, it is necessary to cut a remaining gate of a nozzle portion, and as a cutting method thereof, a method has been proposed that cuts the remaining gate of the nozzle portion by an ultrasonic cutting apparatus including a mechanism for suppressing abnormal vibration (for example, refer to the following Patent Literature 2).

CITATION LIST

Patent Literature

Patent Literature 1: Japanese Patent Laid-Open No. 2016-019619

Patent Literature 2: Japanese Patent Laid-Open No. 2017-177444

SUMMARY OF INVENTION

Technical Problem

Although Patent Literature 1 discloses the container for pre-filled syringe made of a thermoplastic resin and excellent in oxygen barrier properties, a cutting method of the remaining gate of the nozzle portion is not specified.

Although Patent Literature 2 proposes the method of cutting the remaining gate of the nozzle portion by the ultrasonic cutting apparatus including the mechanism for suppressing abnormal vibration, when cut by this method, although it is possible to reduce the generation of burrs to some extent compared with the other known technologies, the generation of burrs cannot be eliminated.

Additionally, since a pointed corner portion is formed in the nozzle portion, there is a possibility that a cap is damaged when the cap is closed, and fragments are generated and mixed into a liquid medicament.

The present invention has been made in view of the above-described circumstances, and an object of the present invention is to provide a manufacturing method of a multilayer syringe barrel that, when the remaining gate of the nozzle portion of the multilayer syringe barrel is cut, does not have burrs and rolled-up parts in a cut surface after cutting, does not generate peeling of the multilayer structure in the nozzle portion, and does not have a pointed corner portion in the nozzle portion that may damage a cap.

Solution to Problem

As a result of diligent consideration, the present inventors have found out that, by performing laser beam irradiation on the corner portion formed in the nozzle portion after cutting the remaining gate of the nozzle portion while vibrating a cutting blade with an ultrasonic cutting apparatus including the mechanism for suppressing abnormal vibration, a multilayer syringe barrel can be obtained that does not have burrs and rolled-up parts in the cut surface after cutting, does not generate peeling of the multilayer structure in the nozzle portion, and does not have a pointed corner portion in the nozzle portion that may damage the cap.

That is, the present invention is as follows.

[1]

A manufacturing method of a multilayer syringe barrel, comprising:

a finish cutting step of cutting a remaining gate of a nozzle portion of the multilayer syringe barrel that is injection-molded from a nozzle tip, with a cutting blade of an ultrasonic cutting apparatus including a mechanism for suppressing abnormal vibration; and an irradiation step of irradiating a laser beam to a corner portion of the nozzle portion, the corner portion being formed in the finish cutting step.

[2]

The manufacturing method of the multilayer syringe barrel according to [1], wherein the finish cutting step comprises:

a partial finish cutting step of cutting a part of the remaining gate of the nozzle portion with the cutting blade in a perpendicular direction to a longitudinal direction of the multilayer syringe barrel; and a complete finish cutting step of relatively rotating the cutting blade and the multilayer syringe barrel, and cutting an uncut portion of the remaining gate of the nozzle portion with the cutting blade in the perpendicular direction to the longitudinal direction of the multilayer syringe barrel.

[3]

The manufacturing method of the multilayer syringe barrel according to [2], wherein the finish cutting step comprises the following steps:

(2-1) a step of moving the cutting blade from an original position to a position that does not enter a nozzle portion inner cavity in the perpendicular direction to the longitudinal direction of the multilayer syringe barrel to cut a part of the remaining gate of the nozzle portion, and returning the cutting blade to the original position;

(2-2) a step of moving the cutting blade from the original position to a predetermined position of the nozzle portion inner cavity in the perpendicular direction to the longitudinal direction of the multilayer syringe barrel to cut a part of the uncut portion of the remaining gate of the nozzle portion, and returning the cutting blade to the original position, while maintaining the cutting blade ultrasonically vibrating, and while maintaining the cutting blade in contact with a nozzle portion cut surface;

(2-3) a step of moving the cutting blade from the original position in the perpendicular direction to the longitudinal direction of the multilayer syringe barrel to cut a part of the uncut portion of the remaining gate of the nozzle portion, and returning the cutting blade to the original position; and (2-4) a step of rotating the multilayer syringe barrel until a positional relationship is established in which the uncut portion of the remaining gate of the nozzle portion does not exist at an intersection point (P1) far from a blade edge, out of two intersection points of a line segment that is perpendicular to the blade edge of the cutting blade and that passes through a center of a nozzle portion cross-sectional outer diameter circle, with the nozzle portion cross-sectional outer diameter circle, and then moving the cutting blade from the original position in the perpendicular direction to the longitudinal direction of the multilayer syringe barrel to cut the uncut portion of the remaining gate of the nozzle portion.

[4]

The manufacturing method of the multilayer syringe barrel according to [3], wherein, in the step (2-2), a moving speed of the cutting blade from the original position to the predetermined position of the nozzle portion inner cavity is 1 mm/s or less, and the predetermined position of the nozzle portion inner cavity is a position separated by a distance of 50% or less of an inner diameter of a nozzle portion cross-sectional inner diameter circle in a direction perpendicular to the blade edge from an intersection point (Q) closer to the blade edge, out of two intersection points of a line segment that is perpendicular to the blade edge of the cutting blade and that passes through a center of the nozzle portion cross-sectional inner diameter circle, with the nozzle portion cross-sectional inner diameter circle.

[5]

The manufacturing method of the multilayer syringe barrel according to [3] or [4], wherein, in the step (2-2), a moving speed of the cutting blade from the predetermined position of the nozzle portion inner cavity to the original position is 1 mm/s or less.

[6]

The manufacturing method of the multilayer syringe barrel according to any of [1] to [5], further comprising a rough cutting step implemented before the finish cutting step, wherein the rough cutting step comprises:

a partial rough cutting step of cutting a part of the remaining gate of the nozzle portion with the cutting blade in a perpendicular direction to a longitudinal direction of the multilayer syringe barrel; and a complete rough cutting step of relatively rotating the cutting blade and the multilayer syringe barrel, and cutting an uncut portion of the remaining gate of the nozzle portion with the cutting blade in the perpendicular direction to the longitudinal direction of the multilayer syringe barrel.

[7]

The manufacturing method of the multilayer syringe barrel according to any of [1] to [6], wherein the finish cutting step is performed n times (n is a positive integer equal to or more than two).

[8]

The manufacturing method of the multilayer syringe barrel according to [7], wherein a load to the cutting blade is 1 to 400 N in an n-th finish cutting step.

[9]

The manufacturing method of the multilayer syringe barrel according to [7] or [8], wherein a distance between a cutting location in an (n−1)-th finish cutting step and a cutting location in an n-th finish cutting step is 0.1 to 1 mm.

[10]

The manufacturing method of the multilayer syringe barrel according to any of [1] to [9], wherein the laser beam in the irradiation step is a carbon dioxide laser.

[11]

The manufacturing method of the multilayer syringe barrel according to any of [1] to [10], wherein an output of the laser beam in the irradiation step is 5 W to 20 W.

Advantageous Effects of Invention

According to the present invention, a multilayer syringe barrel can be manufactured that does not have burrs and rolled-up parts in the cut surface after cutting, does not generate peeling of the multilayer structure in the nozzle portion, and does not have a pointed corner portion in the nozzle portion that may damage the cap.

BRIEF DESCRIPTION OF DRAWINGS

FIG. 1 is a half-cross-sectional view of a multilayer syringe barrel before cutting the remaining gate of a nozzle portion, according to an embodiment of the present invention.

FIG. 2 is an enlarged view of the vicinity of the nozzle portion in the multilayer syringe barrel before cutting the remaining gate of the nozzle portion, according to the embodiment of the present invention.

FIG. 3 is an enlarged view of the vicinity of the nozzle portion in the multilayer syringe barrel before cutting the remaining gate of the nozzle portion, according to the embodiment of the present invention.

FIG. 4 is an enlarged view of the vicinity of the nozzle portion in the multilayer syringe barrel after cutting the remaining gate of the nozzle portion, according to the embodiment of the present invention.

FIG. 5 is a cross-sectional view of a cutting location of the nozzle portion after a partial rough cutting step of cutting a part of the remaining gate of the nozzle portion, according to the embodiment of the present invention.

FIG. 6 is a cross-sectional view of the cutting location of the nozzle portion of the rotated multilayer syringe barrel after the partial rough cutting step of cutting the part of the remaining gate of the nozzle portion, according to the embodiment of the present invention.

FIG. 7 is a cross-sectional view of the cutting location of the nozzle portion after a step (2-1) of cutting a part of the remaining gate of the nozzle portion, according to the embodiment of the present invention.

FIG. 8 is a cross-sectional view of the cutting location of the nozzle portion after a step (2-2) of cutting a part of the remaining gate of the nozzle portion, according to the embodiment of the present invention.

FIG. 9 is a cross-sectional view of the cutting location of the nozzle portion after a step (2-3) of cutting a part of the remaining gate of the nozzle portion, according to the embodiment of the present invention.

FIG. 10 is a cross-sectional view of the cutting location of the nozzle portion of the rotated multilayer syringe barrel after the step (2-3) of cutting the part of the remaining gate of the nozzle portion, according to the embodiment of the present invention.

DESCRIPTION OF EMBODIMENTS

Hereinafter, an embodiment of the present invention will be described based on the drawings. Note that, although a syringe barrel is described as a shape based on the ISO standard in the following embodiment, it is an exemplification for describing the present invention, and the present invention is not limited to the embodiment, and can also be applied to shapes other than the ISO standard.

[Syringe Barrel Shape]

A multilayer syringe barrel 100 shown in FIG. 1 has a standard shape with an internal volume of 5 cc conforming to ISO11040-6. Specifically, the syringe barrel 100 includes a nozzle portion 1 to which a needle can be connected, a shoulder portion 2, and a cylinder portion 3 in this order from a tip side. The cylinder portion 3 consists of a part of the same diameter in the direction of a central axis X-X (the longitudinal direction) of the multilayer syringe barrel 100, and includes a flange 5 in an open end (cylinder portion end 4).

The nozzle portion 1 consists of a part of a smaller diameter than the cylinder portion 3, and is formed into a tapered shape specified by ISO80369-7. The shoulder portion 2 is a part that connects the nozzle portion 1 to the cylinder portion 3 on the opposite side of the cylinder portion end 4. As shown in FIG. 2, the multilayer syringe barrel 100 is injection-molded from the tip side of the nozzle portion 1 by injection-molding from the tip side of the nozzle portion 1, includes a first resin layer (skin layer) 6 consisting of a first thermoplastic resin composition (b), a second resin layer (core layer) 7 consisting of a barrier thermoplastic resin composition (a), and a third resin layer (skin layer) 8 consisting of the first thermoplastic resin composition (b) in this order, and is molded in a manner that leaves a nozzle portion gate by integrally forming the nozzle portion 1, the shoulder portion 2, and the cylinder portion 3. Here, the first resin layer 6 and the third resin layer 8 constitute the outermost layer and the innermost layer of the multilayer syringe barrel 100, respectively, and the second resin layer 7 constitutes a middle layer of the multilayer syringe barrel 100. On the other hand, when injection is performed with the gate position at a location other than the cylinder tip, such as the cylinder portion 3 or the flange portion 5, the second resin layer (core layer) 7 cannot be uniformly formed in the cylinder portion, since welds or gaps are formed, and the like. In the nozzle portion 1, the location (cutting location 9) at which the remaining gate of the nozzle portion is cut is determined, so as to be in the range specified by ISO80369-7. Here, the second resin layer 7 extends from a position closer to the flange 5 than a gasket insertion position in the cylinder portion 3 to a position of the nozzle portion 1.

[Cutting of Remaining Gate of Nozzle Portion]

As shown in FIG. 4, pointed corner portions 10 are formed in the nozzle portion by cutting the remaining gate of the nozzle portion at the cutting location 9 in FIG. 2, by using an ultrasonic cutting apparatus including a mechanism for suppressing abnormal vibration. As the ultrasonic cutting apparatus used in the present invention, a known ultrasonic cutting apparatus can be used as long as a mechanism for suppressing abnormal vibration is provided, and is not limited in any way. Here, abnormal vibration refers to a vibration component in a direction different from the vibration direction parallel to a cutting blade, such as horizontal shaking. When cutting is performed by an ultrasonic cutting apparatus not including a mechanism for suppressing abnormal vibration, heat is easily generated between a blade surface and a resin on an already cut surface at the time of cutting, and not only can the smoothness of the cut surface not secured, but also, when the cutting location has a multilayer structure, the peeling of the multilayer structure and the burrs and rolled-up parts at a cut end caused by the peeling are generated at the time of cutting.

That is, it is considered that a problem occurs when a vibration component in a direction different from the original vibration direction of a vibrator parallel to the cutting blade is applied to the cutting blade. Namely, slight horizontal shaking and the like unrelated to the vibration of a vibrator occur in a resonator body due to a support structure of the resonator and the like, a vibration component in a direction different from the original vibration direction of the vibrator, such as horizontal shaking, in other words, a vibration component in a direction different from the vibration direction parallel to the cutting blade, such as horizontal shaking, is generated in the resonator, and when the vibration component in a direction different from the original vibration direction generated in the resonator, such as horizontal shaking (in the present specification, vibration unrelated to the vibration of the vibrator, such as horizontal shaking, is referred to as "abnormal vibration") is applied to the cutting blade, problems occur, such as blade bending occurring in the cutting blade at the time of cutting of an object, cracking and chipping in a cut piece of the object to be cut caused by the horizontal shaking of a blade edge of the cutting blade due to abnormal vibration, and peeling of the multilayer structure.

Additionally, when the cut angle of the blade edge to the object is not stabilized due to horizontal shaking of the cutting blade, and a slight shift occurs in the contact position of the blade edge of the cutting blade on the object due to the horizontal shaking of the blade edge, there is a possibility that blade bending occurs since the blade edge is cut diagonally into the object, and in this case, although the displacement in the contact position between the blade edge and the object is slight, problems occur, such as the external appearance of a cut surface being worsened since a large positional shift is generated in the cut surface of the object by the cutting blade, and the multilayer structure being easily peeled.

It is preferable for the ultrasonic cutting apparatus to include a mechanism that can raise and lower an ultrasonic cutting blade, and can position a stand on which an object to be cut is placed. It is also preferable for a jig for fixing a syringe barrel to have a structure that supports up to the vicinity of the cutting position of the nozzle portion. An ultrasonic cutting apparatus including a mechanism for suppressing abnormal vibration is described in, for example, Japanese Patent Laid-Open No. 2012-106329, and specifically, the ultrasonic cutter apparatus "UC1000LS" manufactured by Adwelds Co. Ltd. can be listed.

As an example, the apparatus including the mechanism for suppressing abnormal vibration described in Japanese Patent Laid-Open No. 2012-106329 is a vibration cutting apparatus that cuts an object by applying vibration to a cutting blade, characterized by including: a resonator with a vibrator connected to one end, and the cutting blade mounted to a mounting portion of the other end on the opposite side of the vibrator; and a supporting means including a grip portion that grips a gripped portion of the resonator, and supporting the resonator, at least one elongated hole being provided to so as cut through a lateral side of the resonator.

In this vibration cutting apparatus, the resonator is supported by the supporting means since the gripped portion is gripped by the grip portion, and by firmly gripping and supporting the resonator by the grip portion of the supporting means, without interposing a vibration absorption member having elasticity as in conventional methods, it is possible to prevent abnormal vibration in a direction different from the original vibration direction of the vibrator connected to the one end of the resonator from being generated in the resonator, such as horizontal shaking. The ultrasonic cutting apparatus including the mechanism for suppressing abnormal vibration can suppress the peeling of the multilayer structure, and the generation of burrs and rolled-up parts at a cut end.

In order to suppress a syringe barrel from being deformed by heat generated at the time of cutting, it is preferable to select a material having a good thermal conductivity for an ultrasonic cutting blade and a jig, and specifically, aluminum and copper are preferable. Similar to performing rough machining, medium machining, and finish machining in machining by a lathe or the like for shaping into a predetermined shape and for improving the surface smoothness, also in ultrasonic cutting by the ultrasonic cutting apparatus, it is preferable to perform cutting not only at one cutting location (for example, the cutting location 9 in FIG. 2), but also at a plurality of cutting locations (for example, three cutting locations 9 in FIG. 3), since the surface smoothness is improved, and the generation of burrs and rolled-up parts are suppressed. In order to suppress the peeling of the multilayer structure, it is also effective to perform cutting at one cutting location a plurality of times to reduce the load at the time of cutting. Considering the productivity, the number of cutting locations is preferably two to three.

<Initial Cutting (Rough Cutting) Step (1)>

When the number of cutting locations is one, since the volume to be removed is great, a lot of load required for cutting must be applied, and burrs and rolled-up parts are easily generated. Therefore, it is preferable to perform a rough cutting step (1) before a finish cutting step described below.

It is preferable for the rough cutting step (1) to include, a partial rough cutting step (a cut portion 16, an uncut portion 17) of cutting a part of the remaining gate of the nozzle portion with the cutting blade 11 in a perpendicular direction to the longitudinal direction (the X-X direction in FIG. 1) of the multilayer syringe barrel 100 as shown in FIG. 5; and a complete rough cutting step of relatively rotating the cutting blade 11 and the multilayer syringe barrel 100, and then cutting the uncut portion 17 of the remaining gate of the nozzle portion with the cutting blade 11 in the perpendicular direction to the longitudinal direction of the multilayer syringe barrel 100 as shown in FIG. 6.

Note that "relatively rotating the cutting blade and the multilayer syringe barrel" includes the rotation of the multilayer syringe barrel in the circumference direction of the multilayer syringe barrel, the rotations of the cutting blade in the circumference direction of the multilayer syringe barrel, or the combination of these rotations.

<Finish Cutting Step (2)>

After the optionally performed initial cutting step, a finish cutting step is performed. The moment when burrs and rolled-up parts are easily generated at the time of cutting is when the cutting blade comes in contact with an end face. In a case of cutting the remaining gate of the nozzle portion, it is when the cutting blade comes in contact with an internal diameter arc of the nozzle portion, and when the cutting blade comes in contact with an outer diameter arc again after cutting the inner diameter arc.

It is preferable for a finish cutting step (2) to include a partial finish cutting step of cutting a part of the remaining gate of the nozzle portion with the cutting blade in the perpendicular direction to the longitudinal direction of the multilayer syringe barrel; and a complete finish cutting step of relatively rotating the cutting blade and the multilayer syringe barrel, and cutting the uncut portion of the remaining gate of the nozzle portion with the cutting blade in the perpendicular direction to the longitudinal direction of the multilayer syringe barrel. It is preferable to perform the partial finish cutting step a plurality of times.

A more preferable procedure for the finish cutting step (2) is shown below.

<<Step (2-1)>>

In a step (2-1), the cutting blade 11 is moved from an original position to a position that does not enter a nozzle portion inner cavity 13 in the perpendicular direction to the longitudinal direction (the X-X direction in FIG. 1) of the multilayer syringe barrel 100 to cut a part of the remaining gate of the nozzle portion (the cut portion 16, the uncut portion 17), and the cutting blade 11 is returned to the original position (FIG. 7). By stopping the cutting blade 11 at the position that does not enter the nozzle portion inner cavity 13, the generation of burrs and rolled-up parts that may be generated at an inner diameter arc end can be suppressed. It is preferable for the cutting blade stop position in the step (2-1) to be a position separated by the distance of 5% or more (preferably, 5 to 30%) of the outer diameter of the nozzle portion cross-sectional outer diameter circle 14 in the direction perpendicular to the blade edge 12 from an intersection point (P2) closer to the blade edge 12, out of two intersection points of a line segment that is perpendicular to a blade edge 12 of the cutting blade 11 and that passes through the center of a nozzle portion cross-sectional outer diameter circle 14, with the nozzle portion cross-sectional outer diameter circle 14. By stopping the cutting blade 11 at this position, the generation of burrs and rolled-up parts that may be generated in an outer diameter arc end can be suppressed.

<<Step (2-2)>>

In a step (2-2), the cutting blade 11 is moved from the original position to a predetermined position of the nozzle portion inner cavity 13 in the perpendicular direction to the longitudinal direction (the X-X direction in FIG. 1) of the multilayer syringe barrel 100 to cut a part of the uncut portion 17 of the remaining gate of the nozzle portion, and the cutting blade 11 is returned to the original position (FIG. 8), while maintaining the cutting blade 11 ultrasonically vibrating, and while maintaining the cutting blade 11 in contact with the nozzle portion cut surface. When the cutting blade 11 is returned to the original position while maintaining the cutting blade 11 ultrasonically vibrating and while maintaining the cutting blade in contact with the nozzle portion cut surface, since a melted resin that can be burrs and rolled-up parts at the inner diameter arc end is pushed back by a blade surface, and is extended on the cut surface, the generations of burrs and rolled-up parts can be suppressed. From a viewpoint of more efficiently suppressing the generations of burrs and rolled-up parts, the moving speed to return the cutting blade 11 to the original position is preferably 1 mm/s or less, and more preferably 0.5 mm/s or less. Although the lower limit of the moving speed is not particularly limited, the lower limit of the moving speed may be, for example, 0.01 mm/s, 0.05 mm/s, 0.1 mm/s, or the like.

From a viewpoint of more efficiently suppressing the generations of the burrs and rolled-up parts at the inner diameter arc end near the blade edge 12 of the cutting blade 11, in the step (2-2), the moving speed of the cutting blade 11 from the original position to the predetermined position of the nozzle portion inner cavity 13 is preferably 1 mm/s or less, and more preferably 0.5 mm/s or less. Although the lower limit of the moving speed is not particularly limited, the lower limit of the moving speed may be, for example, 0.01 mm/s, 0.05 mm/s, 0.1 mm/s, or the like. It is preferable for the predetermined position of the nozzle portion inner cavity 13 to be a position separated by the distance of 50% or less (specifically, 20 to 50%, preferably, 30 to 40%) of the inner diameter of a nozzle portion cross-sectional inner diameter circle 15 in the direction perpendicular to the blade edge 12 from an intersection point (Q) closer to the blade edge, out of two intersection points of a line segment that is perpendicular to the blade edge 12 of the cutting blade 11 and that passes through the center of the nozzle portion cross-sectional inner diameter circle 15, with the nozzle portion cross-sectional inner diameter circle 15. Alternatively, it is preferable for the predetermined position of the nozzle portion inner cavity 13 to be a position separated by the distance of 30 to 60% (preferably, 40 to 50%) of the outer diameter of the nozzle portion cross-sectional outer diameter circle 14 from the intersection point (P2) in the direction perpendicular to the blade edge 12.

<<Step (2-3)>>

In a step (2-3), the cutting blade 11 is moved from the original position in the perpendicular direction to the longitudinal direction (the X-X direction in FIG. 1) of the multilayer syringe barrel 100 to cut a part of the uncut portion 17 of the remaining gate of the nozzle portion, and the cutting blade is returned to the original position (FIG. 9). It is preferable for the cutting blade stop position in the step (2-3) to be a position separated by the distance of 70 to 95% (preferably, 80 to 90%) of the outer diameter of the nozzle portion cross-sectional outer diameter circle 14 from the intersection point (P2) in the direction perpendicular to the blade edge 12. By stopping the cutting blade 11 at this position, it is possible to suppress deformation or fracture of the uncut portion 17 of the remaining gate of the nozzle portion.

<<Step (2-4)>>

In a step (2-4), the multilayer syringe barrel 100 is rotated until a positional relationship is established in which the uncut portion 17 of the remaining gate of the nozzle portion does not exist at an intersection point (P1) far from the blade edge 12, out of the two intersection points of the line segment that is perpendicular to the blade edge 12 of the cutting blade 11 and that passes through the center of the nozzle portion cross-sectional outer diameter circle 14, with the nozzle portion cross-sectional outer diameter circle 14, and the cutting blade 11 is then moved from the original position in the perpendicular direction to the longitudinal direction (the X-X direction in FIG. 1) of the multilayer syringe barrel 100 to cut the uncut portion 17 of the remaining gate of the nozzle portion (FIG. 10). When the uncut portion 17 of the remaining gate of the nozzle portion exists at the intersection point (P1), the ultrasonic cutting blade 11 drags the melted resin, which tends to cause burrs and rolled-up parts. An angle (S) between the line segment connecting an intersection point (R) far from the blade edge 12 out of two intersection points of an uncut outer diameter arc with its chord to the central point of the nozzle portion cross-sectional outer diameter circle 14, and the line segment connecting the central point of the nozzle portion cross-sectional outer diameter circle 14 to the intersection point (P1) is preferably 60° to 110°, more preferably 70° to 100°, and still more preferably 80° to 90°.

The number of times of performing the finish cutting step (2) may be one, or may be two or more. The number of times of performing the finish cutting step (2) is preferably one to three, and more preferably two. Hereinafter, the finish cutting step (2) performed at the end is also called the final cutting step. In the final cutting step, it is preferable not to apply too much load to the cutting blade. From a viewpoint of suppressing the generation of cracks and melting marks in the cutting location of the nozzle portion, and the peeling of the multilayer structure, the loads applied to the cutting blade is preferably 1 to 400 N, more preferably 10 to 300 N, and particularly preferably 20 to 100 N.

When performing the finish cutting step (2) n times (n is a positive integer equal to or more than two), the distance between the cutting location in the (n−1)-th finish cutting step and the cutting location in the n-th finish cutting step (final cutting step) is preferably 0.01 to 1 mm, and more preferably 0.1 to 1 mm, from a viewpoint of reducing the load required for cutting, and a viewpoint of suppressing the generation of burrs and rolled-up parts.

[Laser Beam Irradiation Step]

In a laser beam irradiation step, a laser beam is irradiated to the corner portion 10 (FIG. 4) of the nozzle portion formed in the finish cutting step (2). Although the irradiation conditions of the laser beam may be appropriately adjusted such that the corner portion 10 can be removed, irradiation with short pulses is preferable to reduce the influence on the surrounding. The type of the laser beam to be irradiated is not particularly limited, and a known laser, for example, a carbon dioxide laser, a YAG laser, a YVO4 laser, or the like can be used. Among these, the carbon dioxide laser is more preferable because of an excellent processability even for a highly transparent resin. From a viewpoint of suppressing the generation of melting marks, the output of the laser beam is preferably 5 W to 20 W.

[Thermoplastic Resin Composition (b)]

A known thermoplastic resin can be appropriately used as the thermoplastic resin used as the thermoplastic resin composition (b) in the skin layers (the first resin layer 6, the third resin layer 8) of the multilayer syringe barrel 100. For the purpose of storing a liquid medicament, a thermoplastic resin with excellent chemical resistance, elution resistance, and shock resistance properties is preferable. It is further preferable to have water vapor barrier properties, and selection may be made from barrier resins that can satisfy 1.0 g·mm/mz·day or less as the numerical value obtained by the technique conforming to JIS K 7126 as for the water vapor permeability. A copolymer made from norbornene and olefins such as ethylene, and a cyclo-olefin copolymer (COC), which is a copolymer made from tetracyclododecene and olefins such as ethylene, are particularly preferable, and a cyclo-olefin polymer (COP), which is a polymer obtained by ring-opening polymerization of norbornene followed by hydrogenation, is also preferable. Such COC and COP are described in, for example, Japanese Patent Laid-Open No. 5-300939 or Japanese Patent Laid-Open No. 5-317411.

[Barrier Thermoplastic Resin Composition (a)]

As the thermoplastic resin used as the barrier thermoplastic resin composition (a) in the core layer (the second resin layer 7) of the multilayer syringe barrel 100, a narrowly defined oxygen barrier thermoplastic resin (so-called passive barrier resin) with properties that simply prevent oxygen permeation may be used, or an oxygen absorbing resin composition (so-called active barrier resin composition) with oxygen absorbing properties, and capable of blocking oxygen permeation to the inside by absorbing the oxygen permeating from the outside may be used. For example, polyester and polyamide can be listed as oxygen barrier thermoplastic resins, and a composition containing a polyester having a tetralin ring and a transition metal catalyst can be listed as oxygen absorbing resin compositions, respectively.

[Manufacturing Method, and the Like]

The manufacturing method of the multilayer syringe barrel 100 in the present embodiment is not particularly limited, and the multilayer syringe barrel 100 can be manufactured by a usual injection molding method. For example, using a molding machine including two or more injection machines and the injection mold, a syringe barrel corresponding to the shape of an injection mold can be manufactured by injecting a barrier thermoplastic resin composition (a) constituting the core layer and a thermoplastic resin composition (b) constituting the skin layer into a cavity via a mold hot runner from respective injection cylinders.

Specifically, the material constituting the skin layer is first injected from the injection cylinder, then the material constituting the core layer is injected from another injection cylinder simultaneously with the resin constituting the skin layer, and a required amount of the resin constituting the skin layer is injected so as to fill the cavity, and thereby the multilayer syringe barrel 100 having the three-layer structure (b)/(a)/(b) can be manufactured.

Example 1

Although the present invention will be described in more detail below by using examples and comparative examples, the present invention is not limited by this in any way. Additionally, in the examples and the comparative examples, various physical property values were measured with the following measuring method and measurement apparatus.

(NMR Measurement)

NMR measurement was performed at room temperature by using Bruker "AVANCE 111-500".

(Cut Surface Inspection)

In the inspection of a cut surface, whether or not burrs exist in the cut surface and the peeling of the multilayer structure were inspected by using a digital microscope (manufactured by KEYENCE CORPORATION, the product name "VHX1000").

Manufacturing Example 1

[Synthesis of Thermoplastic Resin (1)]

In an autoclave with an internal volume of 18 L, 2.20 kg of dimethyl naphthalene-2,6-dicarboxylate, 11.0 kg of 2-propanol, and 350 g of catalyst with 5% palladium supported on activated carbon (50 wt % produce wetted with water) were prepared. Then, after replacing the air in the autoclave with nitrogen, and further replacing nitrogen with hydrogen, hydrogen was supplied until the pressure in the autoclave reached 0.8 MPa. Next, after activating a mixer, adjusting the rotational speed to 500 rpm, and increasing the internal temperature for 30 minutes to reach 100° C., hydrogen was further supplied to make the pressure 1 MPa.

Thereafter, according to the pressure drop due to progress of reaction, supplying of hydrogen was continued so as to maintain 1 MPa. Since there was no more pressure drop after seven hours, after cooling the autoclave and emitting the unreacted residual hydrogen, the reaction liquid was removed from the autoclave. After filtering the reaction liquid, and removing the catalyst, 2-propanol was evaporated with an evaporator from the separated filtrate. 4.40 kg of 2-propanol was added to the obtained crude product, the obtained crude product was purified by recrystallization, and dimethyl tetralin-2,6-dicarboxylate was obtained in 80% yield (yield to dimethyl naphthalene-2,6-dicarboxylate). Note that the analysis results of NMR were as follows. 1H-NMR (400 MHz CDCl3) δ7.76-7.96 (2H m), 7.15 (1H d), 3.89 (3H s), 3.70 (3H s), 2.70-3.09 (5H m), 1.80-1.95 (1H m).

In a polyester resin manufacturing apparatus including a packed column type rectification column, a dephlegmator, a total condenser, a cold trap, a mixer, a heating apparatus, and a nitrogen introduction pipe, 543 g of the above-described dimethyl tetraline-2,6-dicarboxylate, 217 g of ethylene glycol, 0.038 g of polyfunctional compound tetrabutyl titanate, and 0.15 g of zinc acetate were prepared, and the ester exchange reaction was performed by raising the temperature to 230° C. under nitrogen atmosphere. After setting the reaction conversion rate of the dicarboxylic acid component to be 90% or more, temperature raising and depressurizing were gradually performed for 90 minutes, polycondensation was performed at 260° C. and 133 Pa or less for one hour, and a polyester compound containing tetralin rings (the thermoplastic resin (1)) was obtained.

Example 1

[Manufacturing of Multilayer Syringe Barrel]

Using an injection molding machine (manufactured by Sodick Co., Ltd., the model: GL-150), a multilayer syringe barrel having a shape similar to the multilayer syringe barrel 100 in FIG. 1 was manufactured. The shape conformed to the internal volume of 5 mL described in ISO11040-6. Additionally, the molding conditions were adjusted such that the ratio of the core layer resin injection amount to the skin layer resin injection amount is 30 mass %, the beginning of the core layer was located in the range from a rear end of the gasket insertion position to the flange 5, and the termination end of the core layer is located in the range from the shoulder portion to the cutting position of the nozzle portion gate.

First, a multilayer syringe barrel having the three-layer configuration of the thermoplastic resin composition (b)/the barrier thermoplastic resin composition (a)/the thermoplastic resin composition (b) was manufactured by injecting the thermoplastic resin composition (b) constituting the skin layer from an injection cylinder, then injecting a certain amount of the barrier thermoplastic resin composition (a) constituting the core layer from another injection cylinder, then stopping the injection of the barrier thermoplastic resin composition (a), and next, injecting a certain amount of the thermoplastic resin composition (b) to fill the cavity in an injection mold. As the barrier thermoplastic resin composition (a), an oxygen-absorbing composition was used in which cobalt stearate (II) was dry-blended such that the amount of cobalt becomes 0.00025 parts by mass with respect to 100 parts by mass of thermoplastic resin (1). As the thermoplastic resin composition (b), a cyclo-olefin polymer resin (manufactured by Zeon Corporation, the product name "ZEONEX5000", hereinafter written as "COP") was used.

[Cutting of Remaining Gate of Nozzle Portion]

An ultrasonic cutting apparatus "UC1000LS" manufactured by Adwelds Co. Ltd., which is an apparatus including a mechanism for suppressing abnormal vibration, was used for cutting of the remaining gate of the nozzle portion after molding. The cutting was performed such that the shape after the finish cutting (final cutting) step becomes the shape specified by ISO80369-7.

<Initial Cutting (Rough Cutting) Step (1)>

After installing a multilayer syringe barrel (the rotation angle at the time of installation is assumed to be 0°) to the ultrasonic cutting apparatus "UC1000LS", as the first time, a part of the remaining gate of the nozzle portion was cut with the rotation angle of 0° and the cutting stop position located at 50% of the outer diameter, and then the cutting blade was returned to the original position. Then, after rotating the multilayer syringe barrel such that the rotation angle becomes 180°, as the second time, the uncut portion of the remaining gate of the nozzle portion was cut with the cutting stop position located at a position exceeding the outer diameter.

<Finish Cutting Step (2) First Time>

The location moved by 0.5 mm from the above Step (1) was defined as the cutting location. As a step (2-1), a part of the remaining gate of the nozzle portion was cut with the rotation angle of 180° (not rotated after the second time of the initial cutting (rough cutting) step (1)) and the cutting stop position located at 28% of the outer diameter, and then the cutting blade was returned to the original position. Then, as a step (2-2), a part of the uncut portion of the remaining gate of the nozzle portion was cut with the rotation angle of 180° and the cutting stop position located at 45% of the outer diameter. The cutting blade entered the inner cavity, the cutting speed at the time of entry was 0.3 mm/s, and the cutting stop position in the inner cavity (the inner cavity diameter cutting percentage) was located at 37.5% of the inner diameter. Thereafter, the cutting blade was returned to the original position at a speed of 0.3 mm/s, while continuing the vibration of the cutting blade. Subsequently, as a step (2-3), a part of the uncut portion of the remaining gate of the nozzle portion was cut with the rotation angle of 180° and the cutting stop position located at 85% of the outer diameter, and then the cutting blade was returned to the original position. Further, as a step (2-4), the uncut portion of the remaining gate of the nozzle portion was cut with the rotation angle of 52° and the cutting stop position located at a position exceeding the outer diameter, and the cutting blade was returned to the original position.

<Finish Cutting Step (2) Second Time (Final Cutting Step)>

The location moved by 0.2 mm from the above Step (2) First Time was defined as the cutting location. As a step (2-1), a part of the remaining gate of the nozzle portion was cut with the rotation angle of 180° and the cutting stop position located at 28% of the outer diameter, and then the cutting blade was returned to the original position. As a step (2-2), a part of the uncut portion of the remaining gate of the nozzle portion was cut with the rotation angle of 180° and the cutting stop position located at 45% of the outer diameter. The cutting blade entered the inner cavity, the cutting speed at the time of entry was 0.3 mm/s, and the inner cavity diameter cutting percentage was located at 37.5% of the inner diameter. Thereafter, the cutting blade was returned to the original position at a speed of 0.3 mm/s, while continuing the vibration of the cutting blade. Subsequently, as a step (2-3), a part of the uncut portion of the remaining gate of the nozzle portion was cut with the rotation angle of 180° and the cutting stop position located at 85% of the outer diameter, and then the cutting blade was returned to the original position. Further, as a step (2-4), the uncut portion of the remaining gate of the nozzle portion was cut with the rotation angle of 52° and the cutting stop position located at a position exceeding the outer diameter, and the cutting blade was returned to the original position.

<Laser Beam Irradiation Step>

A $CO_2$ laser marker "LP-430U" manufactured by Panasonic Industrial Devices SUNX Co., Ltd. was used for irradiation of a laser beam to the corner portion of the nozzle portion, which was generated by cutting. The irradiation wave length was 10.6 μm, the output was 9 W (30% of the maximum output of the apparatus), the scan speed was 1000 mm/s, and the distance between workpieces was 185 mm, and irradiation was performed on the corner portion under these conditions.

Table 1 shows the cutting conditions describing the cutting speed at the time of entering the inner cavity, the inner cavity diameter cutting percentage at the time of entering the inner cavity, the returning speed of the blade immediately after entering the inner cavity, and whether or not vibration exists when returning the blade immediately after entering the inner cavity at each cutting location, and the cutting stop position (the cutting percentage with respect to the outer diameter of a cut portion) and the rotation angle (the barrel rotation angle when the initial cutting is assumed to be) 0° in each cutting time. The final cutting load was also measured. The cut surface of the multilayer syringe barrel after cutting was inspected, whether or not burrs and rolled-up parts, and multilayer structure peeling exist was checked, and sorting into good products and bad products was performed. The results are shown in Table 2.

Examples 2 and 3

A multilayer syringe barrel was manufactured in a similar manner as in Example 1, except that the cutting conditions were changed to the conditions described in Table 1, and inspection was performed. The results are shown in Table 2.

Example 4

A multilayer syringe barrel was manufactured in a similar manner as in Example 1, except that the laser beam output was set to 6 W (20% of the maximum output), and inspection was performed. The results are shown in Table 2.

Example 5

A multilayer syringe barrel was manufactured in a similar manner as in Example 1, except that the laser beam output was set to 12 W (40% of the maximum output), and inspection was performed. The results are shown in Table 2.

Example 6

A multilayer syringe barrel was manufactured in a similar manner as in Example 1, except that the laser beam output was set to 15 W (50% of the maximum output), and inspection was performed. The results are shown in Table 2.

Example 7

A multilayer syringe barrel was manufactured in a similar manner as in Example 1, except that the laser beam output was set to 18 W (60% of the maximum output), and inspection was performed. The results are shown in Table 2.

Comparative Example 1

A multilayer syringe barrel was manufactured in a similar manner as in Example 1, except that the laser beam irradiation step was removed, and inspection was performed. The results are shown in Table 2.

Comparative Examples 2 and 3

A multilayer syringe barrel was manufactured in a similar manner as in Comparative Example 1, except that the cutting conditions were changed to the conditions described in Table 1, and inspection was performed. The results are shown in Table 2.

TABLE 1

| | | | | | Example 1 | Example 2 | Example 3 | Example 4 | Example 5 | Example 6 |
|---|---|---|---|---|---|---|---|---|---|---|
| Thermoplastic resin a | | | | | | | Thermoplastic resin (1) | | | |
| Cutting step | Initial cutting (rough cutting) step (1) | 1st time | | Rotation angle [°]$^{B)}$ | 0 | 0 | 0 | 0 | 0 | 0 |
| | | | | Cutting stop position$^{4)}$ | 50 | 50 | 50 | 50 | 50 | 50 |
| | | 2nd time | | Rotation angle [°]$^{B)}$ | 180 | 180 | 180 | 180 | 180 | 180 |
| | | | | Cutting stop position$^{4)}$ | More than 100 | More than 100 | More than 100 | More than 100 | More than 100 | More than 100 |
| | | Cutting speed at the time of entering inner cavity [mm/s] | | | 0.4 | 1.5 | 2 | 0.4 | 0.4 | 0.4 |
| | | Inner cavity diameter cutting percentage at the time of entering inner cavity [%] | | | 50 | 50 | 50 | 50 | 50 | 50 |
| | | Returning speed of cutting blade immediately after entering inner cavity [mm/s] | | | 0.4 | 200 | 200 | 0.4 | 0.4 | 0.4 |
| | | Vibration at the time of returning cutting blade immediately after entering inner cavity | | | Yes | No | No | Yes | Yes | Yes |
| | Finish cutting step (2) 1st time | Cutting distance$^{C)}$ [mm] | | | 0.5 | 0.5 | 0.2 | 0.5 | 0.5 | 0.5 |
| | | 1st time | | Rotation angle [°]$^{B)}$ | 180 | 180 | 180 | 180 | 180 | 180 |
| | | | | Cutting stop position$^{4)}$ | 28 | 28 | 28 | 28 | 28 | 28 |
| | | 2nd time | | Rotation angle [°]$^{B)}$ | 180 | 180 | 180 | 180 | 180 | 180 |
| | | | | Cutting stop position$^{4)}$ | 45 | 45 | 45 | 45 | 45 | 45 |
| | | 3rd time | | Rotation angle [°]$^{B)}$ | 180 | 180 | 180 | 180 | 180 | 180 |
| | | | | Cutting stop position$^{4)}$ | 85 | 85 | 85 | 85 | 85 | 85 |
| | | 4th time | | Rotation angle [°]$^{B)}$ | 52 | 52 | 52 | 52 | 52 | 52 |
| | | | | Cutting stop position$^{4)}$ | More than 100 | More than 100 | More than 100 | More than 100 | More than 100 | More than 100 |
| | | Cutting speed at the time of entering inner cavity [mm/s] | | | 0.3 | 0.3 | 0.3 | 0.3 | 0.3 | 0.3 |
| | | Inner cavity diameter cutting percentage at the time of entering inner cavity | | | 37.5 | 37.5 | 37.5 | 37.5 | 37.5 | 37.5 |
| | | Returning speed of cutting blade immediately after entering inner cavity [mm/s] | | | 0.3 | 0.3 | 0.3 | 0.3 | 0.3 | 0.3 |
| | | Vibration at the time of returning cutting blade immediately after entering inner cavity | | | Yes | Yes | Yes | Yes | Yes | Yes |
| | Finish cutting step (2) 2nd time | Cutting distance$^{C)}$ [mm] | | | 0.2 | 0.2 | 0.5 | 0.2 | 0.2 | 0.2 |
| | | 1st time | | Rotation angle [°]$^{B)}$ | 180 | 180 | 180 | 180 | 180 | 180 |
| | | | | Cutting stop position$^{4)}$ | 28 | 28 | 28 | 28 | 28 | 28 |
| | | 2nd time | | Rotation angle [°]$^{B)}$ | 180 | 180 | 180 | 180 | 180 | 180 |

TABLE 1-continued

|  |  |  |  |  |  |  |  |  |
|---|---|---|---|---|---|---|---|---|
|  |  | Cutting stop position[4)] | 45 | 45 | 45 | 45 | 45 | 45 |
|  | 3rd time | Rotation angle [°][B)] | 180 | 180 | 180 | 180 | 180 | 180 |
|  |  | Cutting stop position[4)] | 85 | 85 | 85 | 85 | 85 | 85 |
|  | 4th time | Rotation angle [°][B)] | 52 | 52 | 52 | 52 | 52 | 52 |
|  |  | Cutting stop position[4)] | More than 100 | More than 100 | More than 100 | More than 100 | More than 100 | More than 100 |
|  | Cutting speed at the time of entering inner cavity [mm/s] |  | 0.3 | 0.3 | 0.3 | 0.3 | 0.3 | 0.3 |
|  | Inner cavity diameter cutting percentage at the time of entering inner cavity |  | 37.5 | 37.5 | 37.5 | 37.5 | 37.5 | 37.5 |
|  | Returning speed of cutting blade immediately after entering inner cavity [mm/s] |  | 0.3 | 0.3 | 0.3 | 0.3 | 0.3 | 0.3 |
|  | Vibration at the time of returning cutting blade immediately after entering inner cavity |  | Yes | Yes | Yes | Yes | Yes | Yes |
| Load at the time of final cutting |  |  | 40 | 40 | 80 | 40 | 40 | 40 |
| Angle at the time of final cutting (S) [°] |  |  | 85 | 85 | 85 | 85 | 85 | 85 |
| Laser beam irradiation step |  |  | Yes | Yes | Yes | Yes | Yes | Yes |
| Laser beam output (W) |  |  | 9 W | 9 W | 9 W | 6 W | 12 W | 15 W |

|  |  |  |  | Example 7 | Comparative Example 1 | Comparative Example 2 | Comparative Example 3 |
|---|---|---|---|---|---|---|---|
| Thermoplastic resin a |  |  |  | Thermoplastic resin (1) | | | |
| Cutting step | Initial cutting (rough cutting) step (1) | 1st time | Rotation angle [°][B)] | 0 | 0 | 0 | 0 |
|  |  |  | Cutting stop position[4)] | 50 | 50 | 50 | 50 |
|  |  | 2nd time | Rotation angle [°][B)] | 180 | 180 | 180 | 180 |
|  |  |  | Cutting stop position[4)] | More than 100 | More than 100 | More than 100 | More than 100 |
|  |  | Cutting speed at the time of entering inner cavity [mm/s] |  | 0.4 | 0.4 | 1.5 | 2 |
|  |  | Inner cavity diameter cutting percentage at the time of entering inner cavity [%] |  | 50 | 50 | 50 | 50 |
|  |  | Returning speed of cutting blade immediately after entering inner cavity [mm/s] |  | 0.4 | 0.4 | 200 | 200 |
|  |  | Vibration at the time of returning cutting blade immediately after entering inner cavity |  | Yes | Yes | No | No |
|  | Finish cutting step (2) | Cutting distance[C)] [mm] |  | 0.5 | 0.5 | 0.5 | 0.2 |
|  | 1st time | 1st time | Rotation angle [°][B)] | 180 | 180 | 180 | 180 |
|  |  |  | Cutting stop position[4)] | 28 | 28 | 28 | 28 |
|  |  | 2nd time | Rotation angle [°][B)] | 180 | 180 | 180 | 180 |
|  |  |  | Cutting stop position[4)] | 45 | 45 | 45 | 45 |
|  |  | 3rd time | Rotation angle [°][B)] | 180 | 180 | 180 | 180 |
|  |  |  | Cutting stop position[4)] | 85 | 85 | 85 | 85 |
|  |  | 4th time | Rotation angle [°][B)] | 52 | 52 | 52 | 52 |
|  |  |  | Cutting stop position[4)] | More than 100 | More than 100 | More than 100 | More than 100 |
|  |  | Cutting speed at the time of entering inner cavity [mm/s] |  | 0.3 | 0.3 | 0.3 | 0.3 |
|  |  | Inner cavity diameter cutting percentage at the time of entering inner cavity |  | 37.5 | 37.5 | 37.5 | 37.5 |
|  |  | Returning speed of cutting blade immediately after entering inner cavity [mm/s] |  | 0.3 | 0.3 | 0.3 | 0.3 |
|  |  | Vibration at the time of returning cutting blade immediately after entering inner cavity |  | Yes | Yes | Yes | Yes |
|  | Finish cutting | Cutting distance[C)] [mm] |  | 0.2 | 0.2 | 0.2 | 0.5 |

TABLE 1-continued

|  |  |  |  |  |  |  |  |
|---|---|---|---|---|---|---|---|
| step (2) | 1st time | | Rotation angle [°][B] | 180 | 180 | 180 | 180 |
| 2nd time | | | Cutting stop position[4] | 28 | 28 | 28 | 28 |
| | 2nd time | | Rotation angle [°][B] | 180 | 180 | 180 | 180 |
| | | | Cutting stop position[4] | 45 | 45 | 45 | 45 |
| | 3rd time | | Rotation angle [°][B] | 180 | 180 | 180 | 180 |
| | | | Cutting stop position[4] | 85 | 85 | 85 | 85 |
| | 4th time | | Rotation angle [°][B] | 52 | 52 | 52 | 52 |
| | | | Cutting stop position[4] | More than 100 | More than 100 | More than 100 | More than 100 |
| | | Cutting speed at the time of entering inner cavity [mm/s] | | 0.3 | 0.3 | 0.3 | 0.3 |
| | | Inner cavity diameter cutting percentage at the time of entering inner cavity | | 37.5 | 37.5 | 37.5 | 37.5 |
| | | Returning speed of cutting blade immediately after entering inner cavity [mm/s] | | 0.3 | 0.3 | 0.3 | 0.3 |
| | | Vibration at the time of returning cutting blade immediately after entering inner cavity | | Yes | | | |
| | | Load at the time of final cutting | | 40 | 40 | 40 | 70 |
| | | Angle at the time of final cutting (S) [°] | | 85 | 85 | 85 | 85 |
| | | Laser beam irradiation step | | Yes | No | No | No |
| | | Laser beam output (W) | | 18 W | — | — | — |

[4] Cutting percentage with respect to outer diameter of cut portion
[B] Rotation angle at the time of installation of syringe barrel is assumed to be 0°.
[C] Moving distance of cutting blade in longitudinal direction of syringe barrel from cutting location in previous cutting step

TABLE 2

| | Good product ratio | Number of burrs and rolled-up parts generated | Number of multilayer structure peeling generated | Number of burrs and rolled-up parts, and multilayer structure peeling generated | Number of melting marks generated in corner portion |
|---|---|---|---|---|---|
| Example 1 | 97% | 0% | 3% | 0% | 0% |
| Example 2 | 96% | 0% | 4% | 0% | 0% |
| Example 3 | 95% | 0% | 5% | 0% | 0% |
| Example 4 | 97% | 0% | 3% | 0% | 0% |
| Example 5 | 97% | 0% | 3% | 0% | 0% |
| Example 6 | 97% | 0% | 3% | 0% | 0% |
| Example 7 | 95% | 0% | 3% | 0% | 2% |
| Comparative Example 1 | 90% | 7% | 2% | 1% | —[1] |
| Comparative Example 2 | 88% | 8% | 3% | 1% | —[1] |
| Comparative Example 3 | 85% | 10% | 4% | 1% | —[1] |

[1] Not available since there is no laser irradiation

REFERENCE SIGNS LIST

100: multilayer syringe barrel
1: nozzle portion
2: shoulder portion
3: cylinder portion
4: cylinder portion end
5: flange
6: first resin layer (skin layer)
7: second resin layer (core layer)
8: third resin layer (skin layer)
9: cutting location
10: corner portion formed in nozzle portion
11: cutting blade
12: blade edge
13: nozzle portion inner cavity
14: nozzle portion cross-sectional outer diameter circle
15: nozzle portion cross-sectional inner diameter circle
16: cut portion
17: uncut portion

The invention claimed is:
1. A manufacturing method of a multilayer syringe barrel, comprising:
finish cutting a remaining gate of a nozzle portion of the multilayer syringe barrel that is injection-molded from a nozzle tip, with a cutting blade of an ultrasonic cutting apparatus including a mechanism for suppressing abnormal vibration; and
irradiating a laser beam to a corner portion of the nozzle portion, the corner portion being formed during the finish cutting; wherein the finish cutting comprises:

partial finish cutting a part of the remaining gate of the nozzle portion with the cutting blade in a perpendicular direction to a longitudinal direction of the multilayer syringe barrel, relatively rotating the cutting blade and the multilayer syringe barrel, and complete finish cutting an uncut portion of the remaining gate of the nozzle portion with the cutting blade in the perpendicular direction to the longitudinal direction of the multilayer syringe barrel, wherein the finish cutting further comprises:

(2-1) moving the cutting blade from an original position to a position that does not enter a nozzle portion inner cavity in the perpendicular direction to the longitudinal direction of the multilayer syringe barrel to cut a part of the remaining gate of the nozzle portion, and returning the cutting blade to the original position, (2-2) moving the cutting blade from the original position to a predetermined position of the nozzle portion inner cavity in the perpendicular direction to the longitudinal direction of the multilayer syringe barrel to cut a part of the uncut portion of the remaining gate of the nozzle portion, and returning the cutting blade to the original position, while maintaining the cutting blade ultrasonically vibrating, and while maintaining the cutting blade in contact with a nozzle portion cut surface, (2-3) moving the cutting blade from the original position in the perpendicular direction to the longitudinal direction of the multilayer syringe barrel to cut a part of the uncut portion of the remaining gate of the nozzle portion, and returning the cutting blade to the original position, and (2-4) rotating the multilayer syringe barrel until a positional relationship is established in which the uncut portion of the remaining gate of the nozzle portion does not exist at an intersection point (P1) far from a blade edge, out of two intersection points of a line segment that is perpendicular to the blade edge of the cutting blade and that passes through a center of a nozzle portion cross-sectional outer diameter circle, with the nozzle portion cross-sectional outer diameter circle, and then moving the cutting blade from the original position in the perpendicular direction to the longitudinal direction of the multilayer syringe barrel to cut the uncut portion of the remaining gate of the nozzle portion.

2. The manufacturing method of the multilayer syringe barrel according to claim 1, wherein, in the method (2-2): a moving speed of the cutting blade from the original position to the predetermined position of the nozzle portion inner cavity is 1 mm/s or less, and the predetermined position of the nozzle portion inner cavity is a position separated by a distance of 50% or less of an inner diameter of a nozzle portion cross-sectional inner diameter circle in a direction perpendicular to the blade edge from an intersection point (Q) closer to the blade edge, out of two intersection points of a line segment that is perpendicular to the blade edge of the cutting blade and that passes through a center of the nozzle portion cross-sectional inner diameter circle, with the nozzle portion cross-sectional inner diameter circle.

3. The manufacturing method of the multilayer syringe barrel according to claim 1, wherein, in the method (2-2): a moving speed of the cutting blade from the predetermined position of the nozzle portion inner cavity to the original position is 1 mm/s or less.

4. The manufacturing method of the multilayer syringe barrel according to claim 1, further comprising a rough cutting implemented before the finish cutting, wherein the rough cutting comprises:
partial rough cutting a part of the remaining gate of the nozzle portion with the cutting blade in a perpendicular direction to a longitudinal direction of the multilayer syringe barrel; and relatively rotating the cutting blade and the multilayer syringe barrel, and complete rough cutting an uncut portion of the remaining gate of the nozzle portion with the cutting blade in the perpendicular direction to the longitudinal direction of the multilayer syringe barrel.

5. The manufacturing method of the multilayer syringe barrel according to claim 1, wherein the finish cutting is performed n times and n is a positive integer equal to or more than two.

6. The manufacturing method of the multilayer syringe barrel according to claim 5, wherein a load to the cutting blade is 1 to 400 N during an n-th finish cutting.

7. The manufacturing method of the multilayer syringe barrel according to claim 5, wherein a distance between a cutting location during an (n-1)-th finish cutting and a cutting location during an n-th finish cutting is 0.1 to 1 mm.

8. The manufacturing method of the multilayer syringe barrel according to claim 1, wherein the laser beam during the irradiating is a carbon dioxide laser.

9. The manufacturing method of the multilayer syringe barrel according to claim 1, wherein an output of the laser beam during the irradiating is 5 W to 20 W.

10. The manufacturing method of the multilayer syringe barrel according to claim 1, wherein the multilayer syringe barrel that is manufactured does not have any burrs, and does not have a pointed corner portion in the nozzle portion.

* * * * *